United States Patent
Xiao et al.

(10) Patent No.: US 9,658,171 B2
(45) Date of Patent: May 23, 2017

(54) OPTICAL CARRIER BASED MICROWAVE INTERFEROMETRIC SYSTEM AND METHOD

(71) Applicant: Habsonic LLC, Rolla, MO (US)

(72) Inventors: Hai Xiao, Rolla, MO (US); Jie Huang, Rolla, MO (US); Xinwei Lan, Rolla, MO (US)

(73) Assignee: HABSONIC LLC, Rolla, MO (US)

( * ) Notice: Subject to any disclaimer, the term of this patent is extended or adjusted under 35 U.S.C. 154(b) by 263 days.

(21) Appl. No.: 14/282,919

(22) Filed: May 20, 2014

(65) Prior Publication Data

US 2014/0340671 A1 Nov. 20, 2014

Related U.S. Application Data

(60) Provisional application No. 61/825,295, filed on May 20, 2013.

(51) Int. Cl.
G01B 9/02 (2006.01)
G01N 22/00 (2006.01)
G01L 11/02 (2006.01)
G01M 11/00 (2006.01)

(52) U.S. Cl.
CPC ............ *G01N 22/00* (2013.01); *G01L 11/025* (2013.01); *G01M 11/30* (2013.01)

(58) Field of Classification Search
CPC ............ G01B 9/02007; G01B 9/02029; G01B 9/0203; G01N 21/00; G01N 22/00
See application file for complete search history.

(56) References Cited

U.S. PATENT DOCUMENTS

| 5,822,047 | A | * | 10/1998 | Contarino | G01S 7/484 356/5.01 |
|---|---|---|---|---|---|
| 6,069,686 | A | * | 5/2000 | Wang | G01D 5/266 356/35.5 |
| 7,715,015 | B2 | * | 5/2010 | Waagaard | G01H 9/004 356/484 |
| 8,089,684 | B1 | * | 1/2012 | Koonath | G02F 1/0338 359/237 |
| 2003/0154802 | A1 | * | 8/2003 | Culshaw | D07B 1/145 73/800 |

(Continued)

OTHER PUBLICATIONS

Klevitskiy, B.G. et al. "Microwave Subcarrier Interferometry Methods for Investigating Characteristics of Anisotropic Multimode Lightguides". Journal of Communications Technology and Electronics, 40(13), 1995, pp. 66-72.*

(Continued)

*Primary Examiner* — Michael A Lyons
(74) *Attorney, Agent, or Firm* — Hovey Williams LLP

(57) ABSTRACT

An optical carrier based microwave interferometry (OCMI) system for measuring a physical, chemical, or biological property broadly comprises an optical carrier signal source, a waveguide, a microwave envelope signal source, a microwave modulator, an optical interferometer, a detector, and an analyzer. An optical carrier signal is modulated with a microwave envelope signal and transmitted through an optical interferometer. The optical signal is interrogated in microwave domain to obtain interference patterns or absorption/emission spectra corresponding to the physical, chemical, or biological property being measured.

17 Claims, 11 Drawing Sheets

(56) References Cited

U.S. PATENT DOCUMENTS

2008/0252897 A1* 10/2008 Arnvidarson ............ G01J 3/45
356/452
2012/0262190 A1* 10/2012 Kondo ............... G01N 21/3581
324/639

OTHER PUBLICATIONS

Winnall, S.T. et al. "A Fabry-Perot Scanning Receiver for Microwave Signal Processing". IEEE Transactions on Microwave Theory and Techniques, vol. 47, No. 7, Jul. 1999, pp. 1385-1390.*
Johnstone, Alan et al. "Dynamic displacement measurements with sub-micron resolution using microwave sub-carrier interferometry".*

* cited by examiner

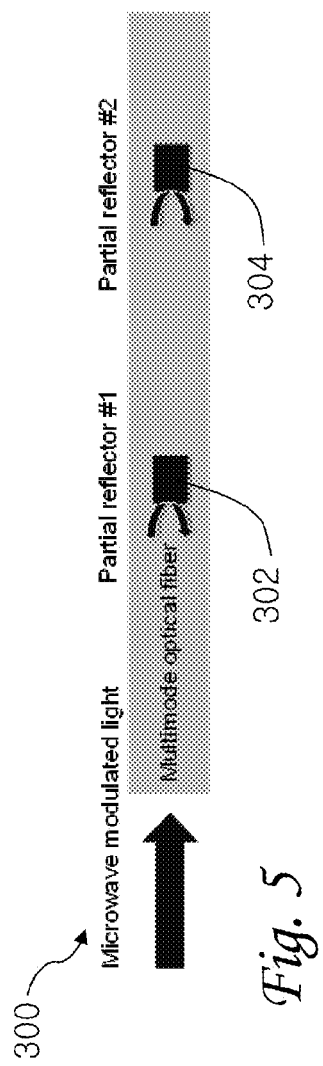
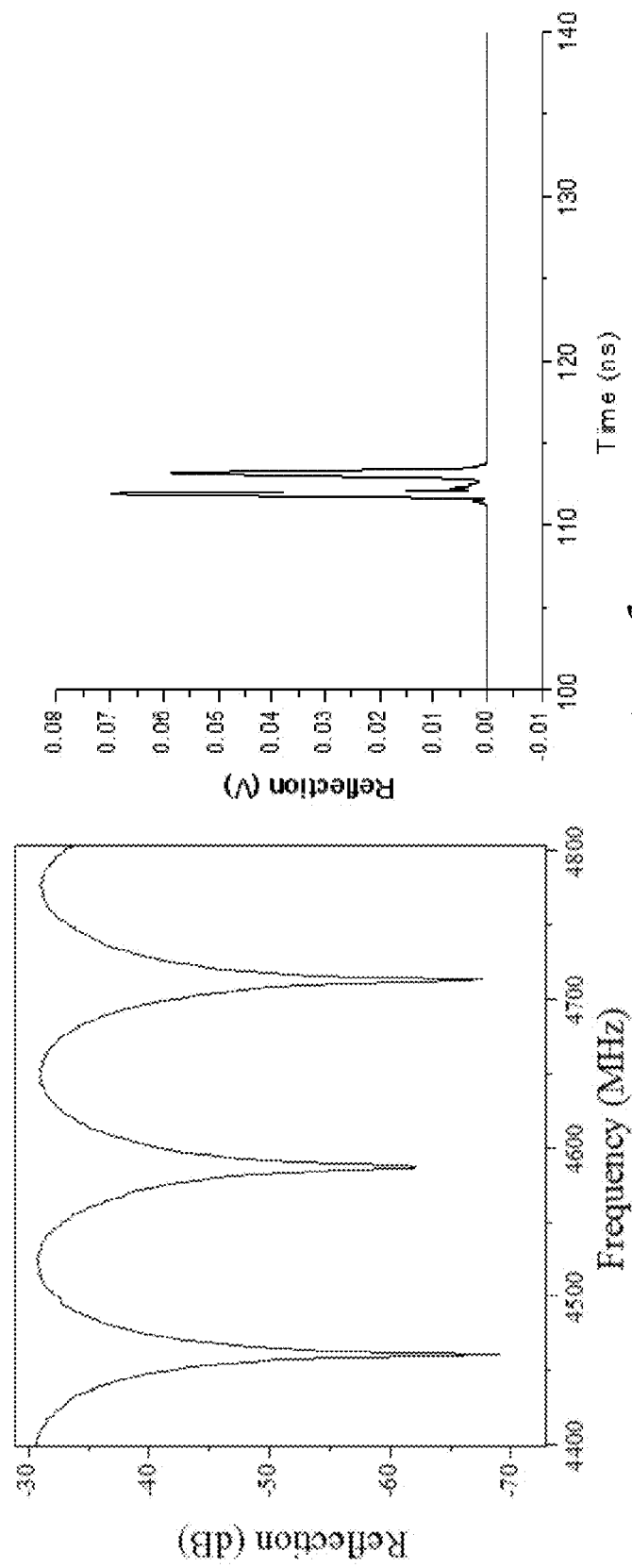
Fig. 5
Fig. 6a
Fig. 6b

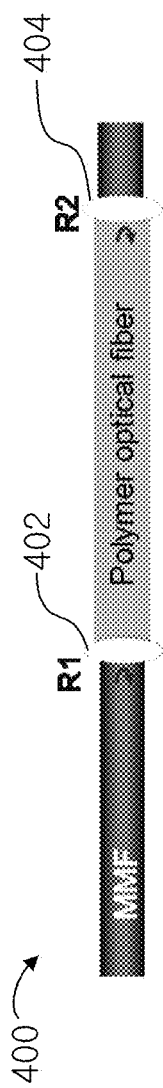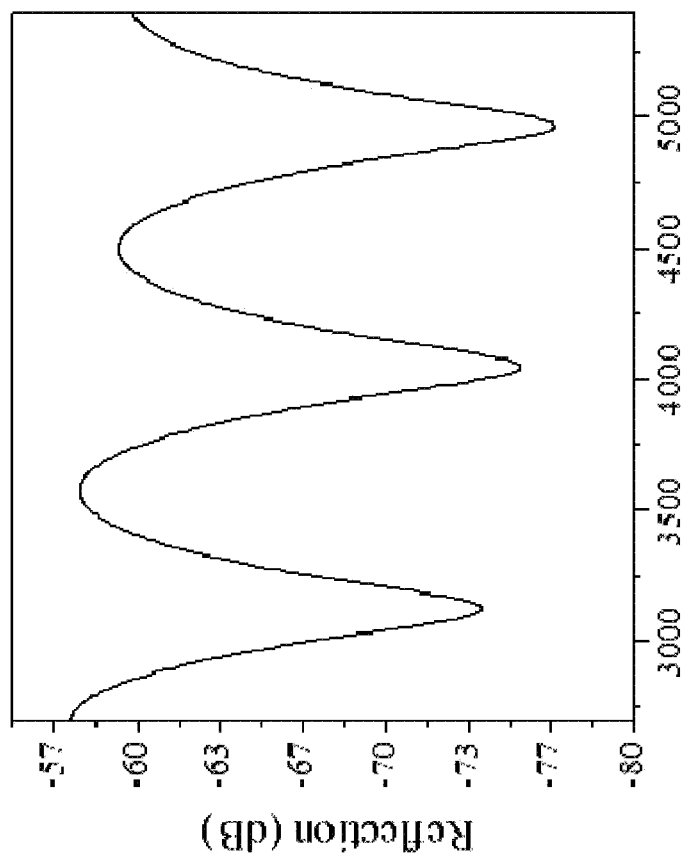
Fig. 7
Fig. 8a

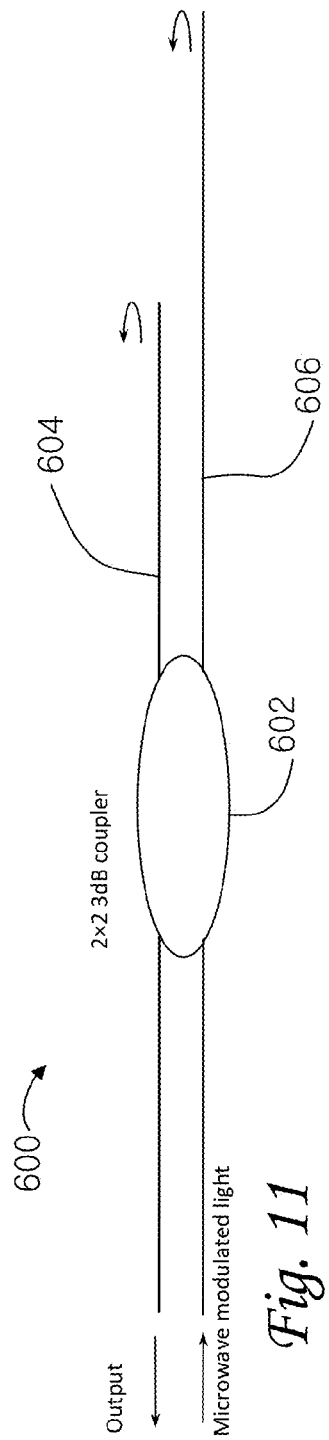
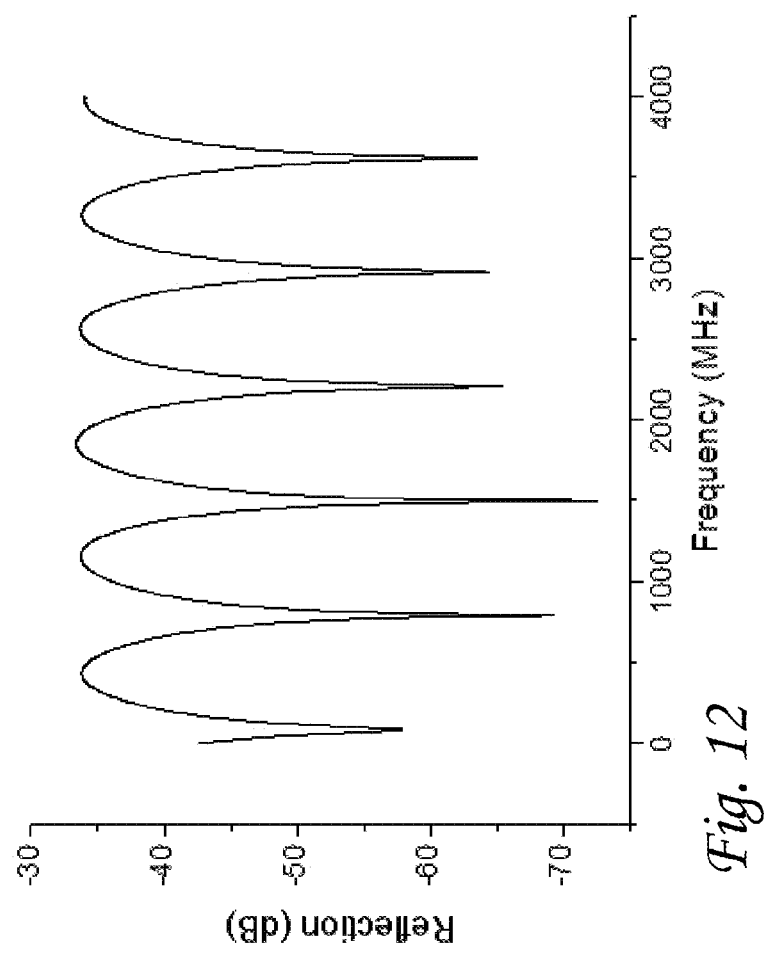
Fig. 11
Fig. 12

OPTICAL CARRIER BASED MICROWAVE INTERFEROMETRIC SYSTEM AND METHOD

RELATED APPLICATION

The present application is a non-provisional patent application and claims priority benefit, with regard to all common subject matter, of earlier-filed U.S. provisional patent application titled "Optical Carrier Based Microwave Interferometric Sensors", Ser. No. 61/825,295, filed May 20, 2013, incorporated by reference in its entirety into the present document.

BACKGROUND

Optical interferometry has been widely used for accurate measurement of various physical, chemical and biological quantities. Optical interference superposes two or more coherent optical waves of certain propagation delays to generate periodic patterns in time, space, or frequency domain. The information embedded in the periodic patterns such as the phase, the amplitude, and the frequency positions of the waves can be utilized to compute the propagation delays. An interferometer can be designed to encode the information to be measured into the propagation delays. Thus, an interferometric sensor can be used to measure various parameters. Optical interferometric sensors and measurement techniques have high sensitivity, high response frequency, immunity to electromagnetic interference (EMI), remote operation, low optical attenuation and the ability to be transmitted over the long distance.

The principle has been implemented into various sensors and instruments. Based on the different ways of generating, separating, and combining the coherent optical waves, various types of optical interferometers have been implemented into optical interferometric systems including the Fabry-Perot interferometer (FPI), Fizeau interferometer, Michelson interferometer (MI), Mach-Zehnder interferometer (MZI) and Sagnac interferometer. These interferometers have found a wide variety of applications in various scientific and engineering fields.

Although optical interference and optical interferometers have many uses, they have also shown certain limitations such as the limited dynamic range, high-cost of implementation, stringent requirements on surface qualify and fabrication precision, difficulty to be multiplexed, and strong dependence on the material and geometry of the optical waveguides. As a result, optical interferometers have limited field applications despite their wide usage in laboratory conditions and controlled environments.

Microwave interferometers alleviate some of the limitations of optical interferometers. For example, construction of a microwave interferometer does not necessarily require a manufacturing accuracy as high as that in an optical interferometer. In addition, the stringent requirements on optical waveguides (e.g., geometry, dispersion, modes, and material characteristics) for making an optical interferometer can be relieved significantly in microwave interferometers.

However, microwaves cannot transmit over a long distance in a waveguide because of the large dielectric loss of the medium used for construction of the waveguide. Meanwhile, microwave waveguides are usually large in size (e.g., the most commonly used coaxial cable has a typical diameter on the order of several millimeters). In addition, pure microwave interferometers are susceptible to electromagnetic interference (EMI). As a result, pure microwave interferometers also have limited applications, especially when used as a sensor.

SUMMARY

The present invention solves the above-described problems and provides a distinct advance in the art of interferometry by using microwave photonics to bring together the strengths of optics and microwaves. More particularly, the present invention provides an interferometry system that modulates optic waves with a microwave signal and processes the signal in microwave and optical domain to measure physical, chemical, and biological properties via interference patterns in the microwave frequency range.

Optics and microwaves are governed by the same electromagnetic theories but they occupy drastically different spectral regions. The two have many characteristics in common but significant differences in properties and applications. In optical interference, a photodetector is not fast enough to resolve the oscillations in the very high optical frequency. On the other hand, microwave interference can be resolved within its fundamental oscillation frequency. Two microwave beams can also be coherently superimposed to generate an interference pattern similar to two optical beams. By modulating optical waves with a microwave signal, the microwave envelope-modulated optical waves can be sent through an optical waveguide (e.g., an optical fiber) to reach a long distance and then interrogated in the microwave spectrum.

An embodiment of the present invention is an optical carrier based microwave interferometry (OCMI) system for measuring a physical, chemical, or biological property. The system broadly comprises an optical carrier signal source, a waveguide (or freespace or other medium), a microwave envelope signal source, a microwave modulator, an optical interferometer, a detector, and an analyzer.

The optical carrier signal source generates a first optical carrier signal and transmits it along a first path of the waveguide. The optical carrier signal source may be a low coherence broadband light source, a laser, or other suitable electromagnetic wave generator.

The envelope signal source generates a first microwave envelope signal and may be a microwave source or other suitable source configured to generate electromagnetic waves in the low frequency large wavelength band.

The microwave modulator modulates the first optical carrier signal with the first microwave envelope signal and may be an electro-optic modulator (EOM), an amplitude modulator, phase modulator, frequency modulator, or any other suitable modulator.

The optical interferometer splits the first optical carrier signal and the first microwave envelope signal into at least second and third optical carrier signals and second and third microwave envelope signals. The second signals travel along a second path and the third signals travel along a third path in the optical interferometer. The second signals and the third signals then interfere with each other in a fourth path to form a fourth optical carrier signal and a fourth microwave envelope signal. Inside the optical interferometer, the second and third paths have different lengths which generate propagation delays between the second carrier and envelope signals and the third carrier and envelope signals. The difference in length between the second and third paths is defined as the optical path difference (OPD). In most embodiments, the OPD of the optical interferometer is longer than the coherence length of the optical carrier signal source but shorter than the coherence length of the microwave envelope signal source. As such, the optical carrier signals build up incoherently in the fourth path while the microwave envelope signals build up coherently to form an amplitude pattern in microwave domain.

The detector converts the fourth microwave envelope signal into an electrical signal and may be a high speed photodetector or any other suitable electromagnetic detector. The detector has a limited bandwidth so that only the microwave modulation can be determined.

The analyzer extracts amplitude patterns and other wave features from the electronic signal over the frequency range of the microwave envelope signal that correspond to values of the physical, chemical, or biological property being measured and displays them in an interferogram. One way to obtain the interferogram in microwave domain is to sweep the frequency of the microwave envelope signal and record the demodulated microwave signal via the photodetector. The OCMI system, now interrogated in microwave domain, can be used for sensing by correlating its OPD to the physical, chemical, or biological property being measured.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 5 is an elevation view of a multimode optical fiber Fabry-Perot interferometer;

FIG. 6a is an interferogram of a multimode optical fiber Fabry-Perot OCMI system;

FIG. 6b is a graph of a reflected optical carrier signal in time domain after a complex inverse Fourier transform is applied to the microwave envelope signal;

FIG. 7 is an elevation view of a polymer optical fiber Fabry-Perot interferometer;

FIG. 8a is an interferogram of a polymer optical fiber Fabry-Perot OCMI system;

FIG. 11 is a schematic view of a Michelson interferometer;

FIG. 12 is an interferogram of a Michelson OCMI system;

Figure 1:
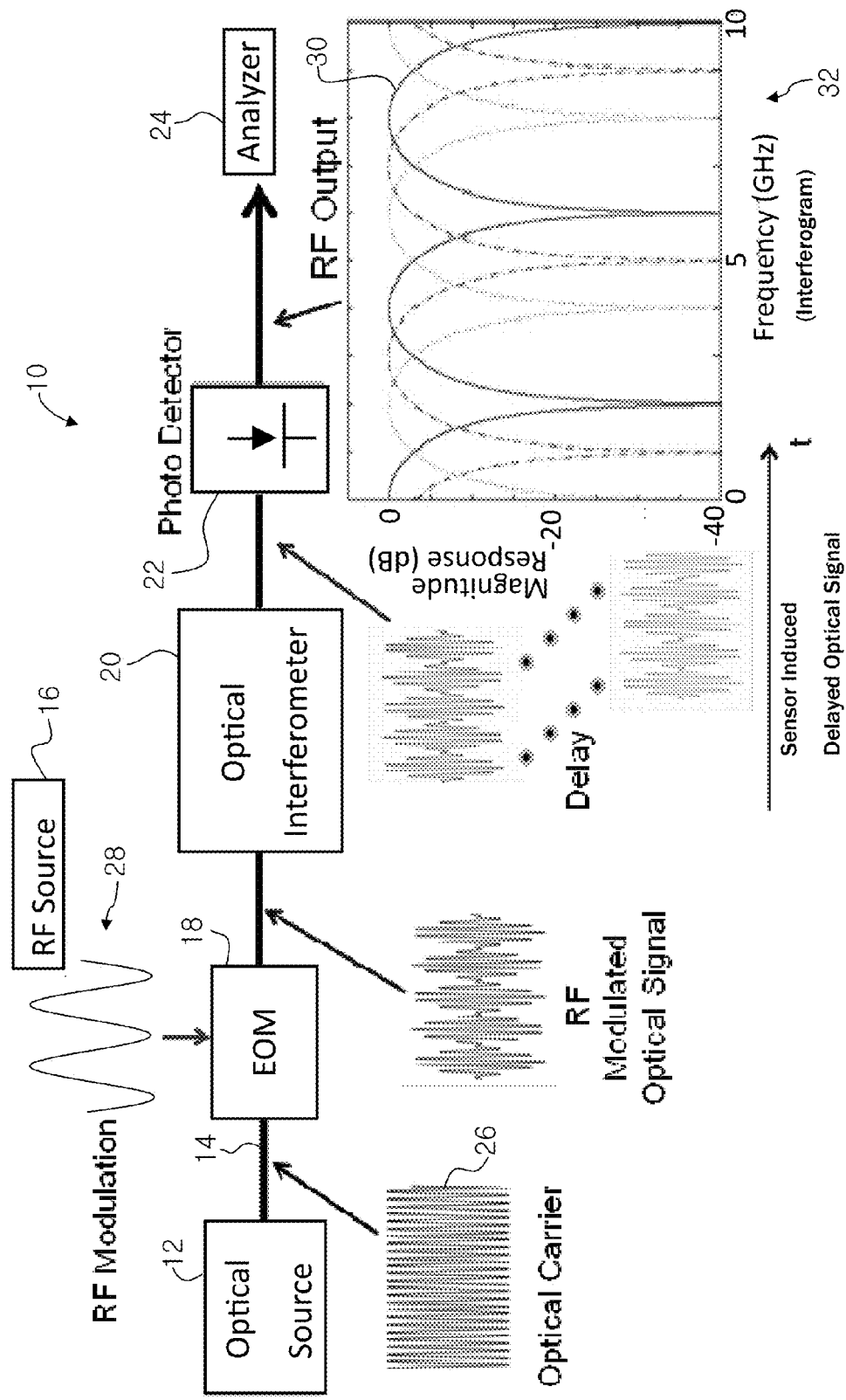
FIG. 1 is a schematic view of an optical carrier based microwave interferometry (OCMI) system.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Turning now to the drawings figures, and particular FIG. 1, an optical carrier based microwave interferometric (OCMI) system 10 for measuring a physical, chemical, or biological property is illustrated. The OCMI system 10 broadly comprises an optical carrier signal source 12, a waveguide 14, a microwave envelope signal source 16, a microwave modulator 18, an optical interferometer 20, a detector 22, and an analyzer 24.

The optical carrier signal source 12 generates an optical carrier signal 26 and transmits it along a path of the waveguide 14. The optical carrier signal source 12 may be a low coherence broadband light source, a laser, or other suitable electromagnetic wave generator.

The wave guide 14 is an optical fiber cable or similar medium as described above. Alternatively, the signals may travel in freespace (e.g., a vacuum, gas, liquid, solid, and biological material).

The envelope signal source 16 generates a first microwave envelope signal 28 and may be a microwave source or other suitable source configured to generate electromagnetic waves in the low frequency large wavelength band. The envelope signal source 16 may be part of a vector network analyzer device.

The microwave modulator 18 modulates the first optical carrier signal 26 with the first microwave envelope signal 28 and may be an electro-optic modulator (EOM), an amplitude modulator, DC modulator, or any other suitable modulator.

The optical interferometer 20 introduces a delay in the optical carrier signal, which creates coherent interference in the microwave domain. The optical interferometer 20 may be an intrinsic or extrinsic Fabry-Perot interferometer (FPI), Fizeau interferometer, Michelson interferometer (MI), Mach-Zehnder interferometer (MZI) and Sagnac interferometer, or any other suitable interferometer, as described in detail below.

The detector 22 converts the microwave-modulated optical carrier signal into an electrical signal and may be a high speed photodetector or any other suitable electromagnetic detector. The detector 22 has a limited bandwidth so that only the microwave modulation can be determined.

The analyzer 24 extracts amplitude patterns, phase patterns, and other wave features 30 in the microwave domain from the electronic signal that correspond to values of the physical, chemical, or biological property being measured and displays them in an interferogram 32. One way to obtain the interferogram 32 in microwave domain is to sweep the frequency of the microwave envelope signal 28 and record the demodulated microwave signal via the photodetector 22. The OCMI system 10, now interrogated in microwave domain, can be used for sensing by correlating its OPD to the property of interest. It will be understood that carrier signal frequencies outside of the visible light range such as infrared and ultraviolet frequencies and envelope signal frequencies outside of the microwave range may be used in the OCMI system 10.

An OCMI system 100 constructed in accordance with another embodiment of the invention includes a broadband light source 102, an electro-optic modulator 104, a polarizer 106, a polarization controller 108, a vector network analyzer 110, an RF microwave source 112, an RF amplifier 114, a DC biaser 116, an optical interferometer 118, an optical circulator 120, a high speed photodetector 122, an RF amplifier 124, and a DC filter 126.

The broadband light source 102 generates a first optical carrier signal and is used to minimize the coherence length of the first optical carrier signal.

The electro-optic modulator (EOM) 104 amplitude modulates the first optical carrier signal and is driven by port 1 of a vector network analyzer (VNA, e.g., HP 8753es) 110. An alternative way to modulate the first optical carrier signal would be to use direct current modulation by changing the driving current of a semiconductor laser or LED using a microwave signal.

The polarizer 106 and the polarization controller 108 are optional and can be placed before the EOM 104 to enhance the modulation efficiency or modulation depth.

The RF microwave source 112 from port 1 could be amplified first via the RF amplifier 114 and then biased by the DC power (~1.6V) biaser 116 before it inputs to the EOM 104 to obtain a maximum modulation index.

The optical interferometer 118 (e.g., an optical fiber interferometer) receives the modulated light (the first optical carrier signal and the first microwave envelope signal) via the optical circulator 120 (alternatively, a fiber coupler can also be used). The optical interferometer 118 splits the first optical carrier signal and the first microwave envelope signal into at least second and third optical carrier signals and second and third microwave envelope signals. The second signals travel along a second path and the third signals travel along a third path in the optical interferometer 118. The second signals and the third signals then interfere with each other in a fourth path to form a fourth optical carrier signal and a fourth microwave envelope signal. Inside the optical interferometer 118, the second and third paths have different lengths which generate propagation delays between the second carrier and envelope signals and the third carrier and envelope signals. The optical path difference (OPD) corresponds to the difference in length between the second and third paths. In most embodiments, the OPD of the optical interferometer 118 is longer than the coherence length of the optical carrier signal source but shorter than the coherence length of the microwave envelope signal source. As such, the optical carrier signals build up incoherently in the fourth path while the microwave envelope signals build up coherently to form an amplitude pattern in microwave domain.

The high speed photodetector 122 receives the reflected signals from the optical interferometer 118 and converts the light signal into an RF analog signal. The output signal from the photodetector 122 can be further amplified by the optional microwave amplifier 124.

The DC filter 126 connects the photodetector 122 (or the optional microwave amplifier) to port 2 of the vector network analyzer 110. By sweeping the modulation frequencies of the microwave signal, the amplitude and phase of the signal passing through the optical interferometer 118 is recorded. The recorded signal ($S_{21}$, the scattering parameter of the VNA 110 including amplitude and phase information in this case) is the microwave interference spectrum of the sensor.

Embodiments of the present invention utilizing various optical interferometers (FPI, MI, MZI, etc.) will now be described in detail. It is necessary to note that although fiber optic interferometers are used here for the purpose of demonstration of the invention, optical interferometers in the form of bulk optics can also be implemented.

Example 1

OCMI Based Fabry Perot Interferometry System

Optical fiber based Fabry-Perot Interferometers (FPI) have been widely used in optic-only interferometry. In a conventional configuration, FPIs can be simply constructed by two endface-cleaved optical fibers. The two reflections at the two end surfaces of the two fibers form a Fabry-Perot (FP) cavity which generates an interference pattern when interrogated by an analyzer. The interferogram can be recorded by the analyzer to calculate the length and/or the refractive index of the cavity. The length of a conventional all-optical FP cavity is in tens of micrometers so that the interferogram of the FPI is optimally resolved via optical instrumentation. However, as mentioned previously, the surfaces used to construct an all-optical FPI needs to be very smooth, i.e., optical grade with a surface roughness smaller than 1/20 of the optical wavelength, or about 50 nm. In addition, the two endfaces of the FPI cavity needs to be in almost perfectly parallel to obtain a high-quality (i.e., good fringe visibility) interference signal in optical domain.

Up-to-date, most of the optical fiber FPIs are made using single mode optical fibers. Although multimode optical fibers have been used to construct FPIs, they were found to have poor interference signal (i.e., low fringe visibility) due to the modal noise or modal interferences as a result of different paths of the vast number of optical modes supported by a multimode fiber.

Figure 2:
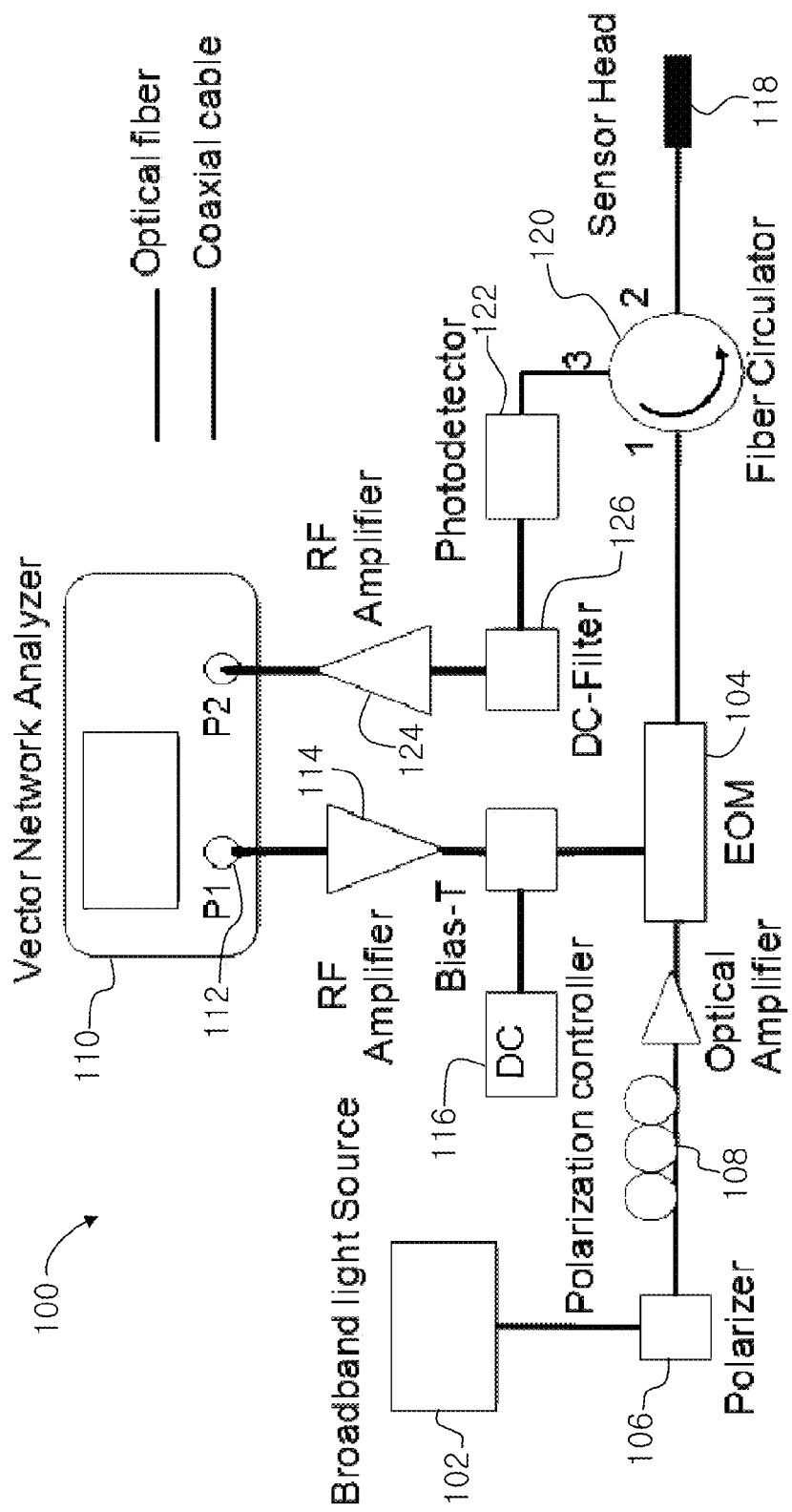
FIG. 2 is a schematic view of an example apparatus to realize the OCMI system of FIG. 1.
Figure 3:
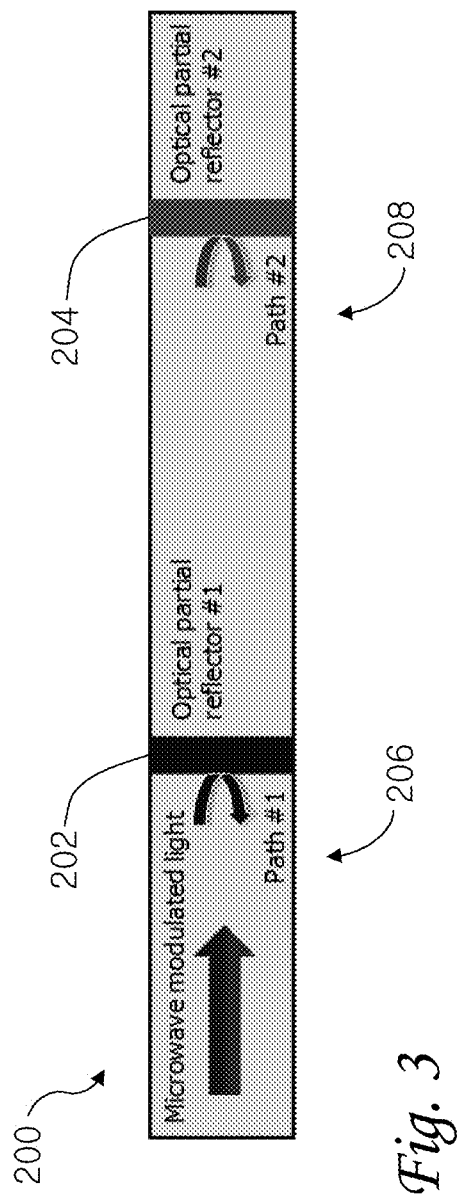
FIG. 3 is an elevation view of a Fabry-Perot interferometer.

A Fabry-Perot interferometer (FPI) 200 can be used to construct an OCMI-FPI system, as illustrated in FIG. 3. In the OCMI-FPI system, two consecutive optical partial reflectors 202, 204 are created along an optical waveguide. It is worth noting that more than two partial reflectors can be implemented along the same waveguide. The optical waveguide can be an optical fiber or other forms and can be single mode, multimode, cladded, and uncladded. The microwave modulated light travels along the waveguide and is partially reflected at the two optical particle reflectors 202, 204. The two reflected beams have different optical paths 206, 208 with an OPD between them. The OPD is larger than the coherence length of the optical carrier source but smaller than the coherence length of the microwave signal used to modulate the optical carrier signal. As a result, the two reflected beams superimpose incoherently in optical domain but coherently in microwave domain. When observed using the described OCMI setup in FIG. 2, the interference signal can be observed in microwave domain.

The wavelength of the microwave signal is much larger than that of the optical signal. The OPD of the OCMI-FPI system 200 is in tens of millimeters, which is also much larger than that of an all-optical interferometer system. The qualities of the optical components and accuracy of assembly therefore do not need to be as precise as an all-optical interferometry system.

1) Single Mode Optical Fiber OCMI-FPI System

Figure 4A:
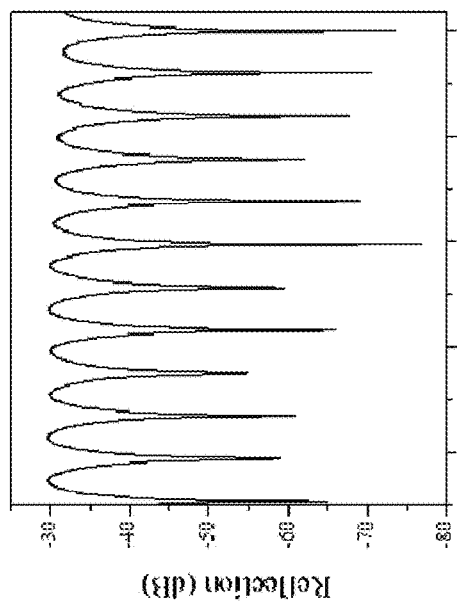
FIG. 4a is an interferogram of an OCMI system with an observation bandwidth of 2 GHz.
Figure 4C:
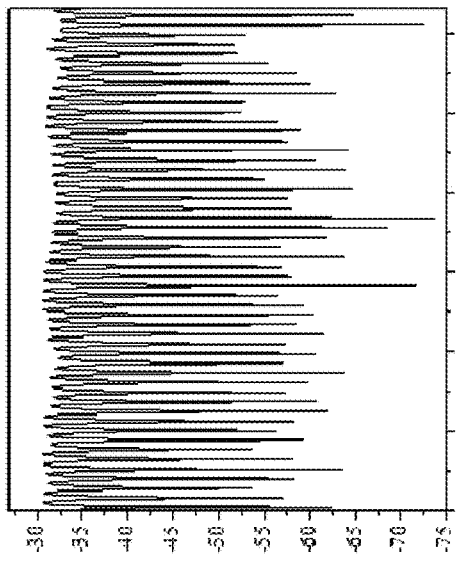
FIG. 4c is another interferogram of an OCMI system, the interferogram showing a frequency shift due to a sensed change in axial strain.
Figure 4B:
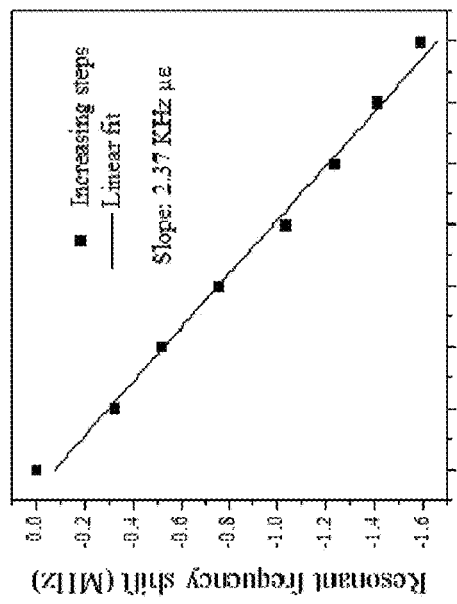
FIG. 4b is another interferogram of an OCMI system with an observation bandwidth of 0.5 GHz.

A single mode OCMI-FPI system may be constructed using single mode fibers, as shown in FIG. 3. In this embodiment, two optical partial reflectors are implemented using cleaved optical endfaces where the optical reflections are generated at the interface between the optical fiber and air. The distance between the optical reflectors is 2 meters in this example. The interference spectrum of the single mode fiber OCMI-FPI system is obtained using the setup illustrated in FIG. 2. FIGS. 4a and 4b show the interferogram of the single mode fiber OCMI-FPI system in microwave spectrum domain with the observation bandwidth of 2 GHz and 0.5 GHz, respectively. The fringe visibility is over 30 dB and the free spectral range of the interferogram is about 40 MHz.

Figure 4D:
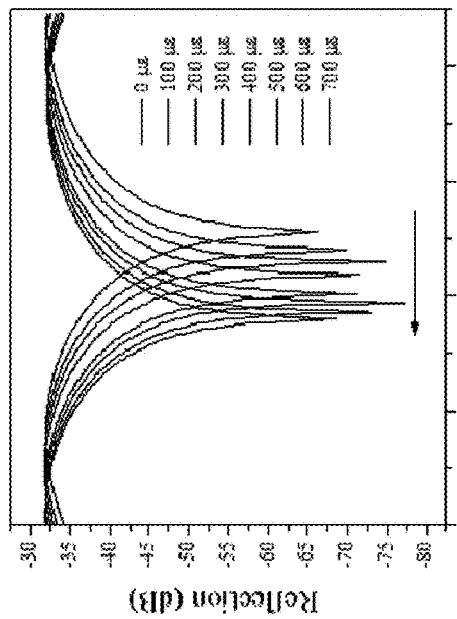
FIG. 4d is a graph showing a linear relation between frequency shift and strain.

The present invention can be used to measure various physical, chemical, and biological properties, as mentioned above. Example properties include displacement, strain, temperature, pressure, acoustic/ultrasonic waves, refractive index, liquid level, gas or vapor concentration, biological quantity, etc. The OCMI-FPI system is used as an axial strain sensor to demonstrate the measuring capabilities of the present invention. Optical fiber is tightly fixed on to two translation stages leaving the OCMI-FPI interferometer between the two fixing points. By moving the translation stages, an axial strain is applied to the fiber and thus to the OCMI-FPI interferometer. As a result, the interferometer is elongated as the translation stages are moved. The resultant interferograms at different applied axial strains are seen in FIG. 4c. The frequency shift of a specific interference valley as a function of the applied axial strain at a step of $100\mu\varepsilon$ is seen in FIG. 4d. The frequency shift—applied strain shows a monotonic linear relation with a slope of 2.37 kHz/$\mu\varepsilon$, which is the sensitivity of the OCMI-FPI system when used as a strain sensor.

2) Multimode Optical Fiber Based OCMI-FPI System

Multimode optical fibers (MMFs) are used in sensing applications and high power lasing systems because of the large core size, easy coupling of light into the fiber, and the ability to deliver a high optical power. However, multimode fibers are difficult to use in constructing optical interferometers due to the large modal dispersion and the multimode interference (MMI) induced noise and lowered fringe visibility. The multimodal interference becomes even worse in some special optical fibers, such as the uncladded sapphire fiber or polymer optical fiber. However, these special fibers have some unique properties that make them useful for specific applications. For example, single crystal sapphire fibers have a melting point exceeding 2000° C., which makes them very useful for sensing applications in high temperature harsh environments. Polymer optical fibers, also known as plastic optical fibers, are flexible and can survive much larger axial strain than the glass fibers. As a result, polymer optical fibers can be used for sensing large strains and can find many applications in structural health monitoring.

As mentioned previously, the present invention is insensitive to the multimodal interference and therefore could be used even if the optical interferometer is constructed by multimode fibers (FIG. 5). This is because the MMI effects from the optical carrier waves will not influence the microwave envelope signals. The phase of the microwave envelop signals are thus stable enough for coherent superposition. To demonstrate the insensitivity of the present invention to multimode interference, a multimode optical fiber (MMF) based OCMI-FPI system is constructed, which has the same structure of the single mode fiber OCMI-FPI system except that the waveguide is replaced by a MMF with core and cladding diameters of 105 $\mu$m and 125 $\mu$m, respectively. An interferometer 300 of a MMF based OCMI-FPI system having two reflectors 302, 304 is constructed in the same way as in the single mode fiber interferometer. The distance between the two reflectors 302, 304 is about 14 cm in this example. The microwave interferogram of the MMF based OCMI-FPI system is interrogated using the setup illustrated in FIG. 2 to generate the microwave interferogram shown in FIGS. 6a and 6b.

A complex and inverse Fourier transfer is applied to the interference spectrum shown in the microwave interferogram in FIG. 6a. The result is the time domain reflectometry of the MMF based OCMI-FPI system 300, as shown in FIG. 6b. The two reflectors along the fiber can be clearly identified in time domain. It is the coherent superposition of these two reflections that introduces the interference pattern in frequency domain as shown in FIG. 6a. The time domain reflectometry also reveals that the key to obtaining a large fringe visibility of the interference signal is to have an equal amplitude of the two reflections.

Figure 8C:
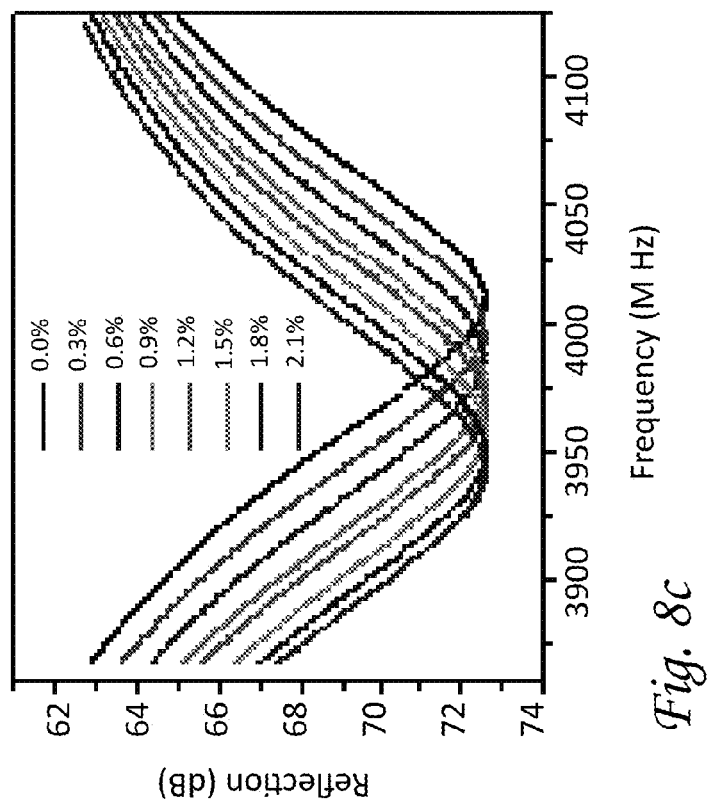
FIG. 8c is a graph showing the frequency shift of FIG. 8b.
Figure 8B:
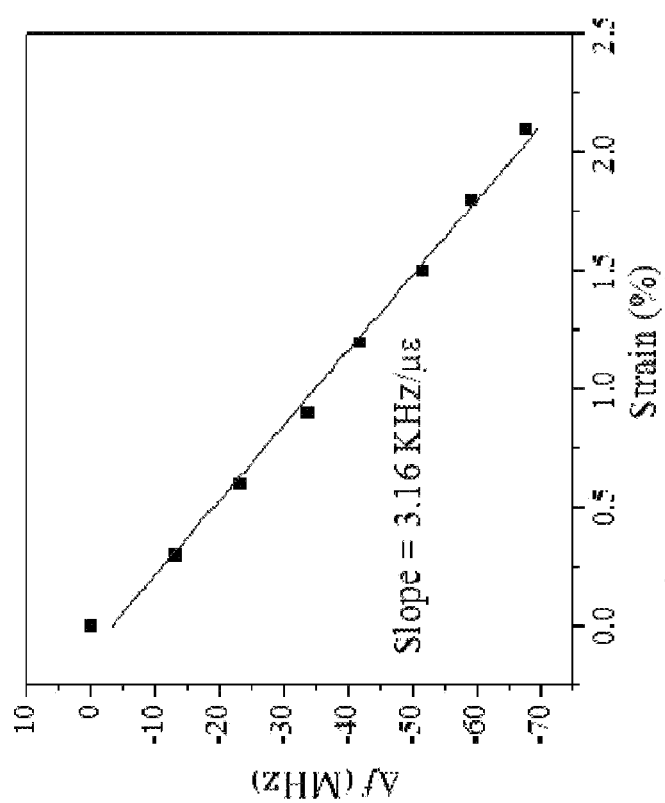
FIG. 8b is a graph showing a linear relation between frequency shift and strain measured by a polymer optical fiber Fabry-Perot OCMI system.

The present invention may also use special optical fibers including sapphire optical fiber and polymer optical fiber. An interferometer 400 of a polymer optical fiber based OCMI-FPI system is shown in FIG. 7. The first reflector 402 is created by the refractive index mismatch between the silica glass fiber and the polymer fiber. The second reflector 404 is created at the interface between the polymer fiber and the air at the far end. The interference spectrum of the polymer fiber OCMI-FPI system in the microwave domain is shown in FIG. 8. The fringe visibility is larger than 20 dB and the free spectral range is around 750 MHz. The polymer fiber OCMI-FPI system responds to applied axial strain, where the frequency shift of the interferogram is a linear function of the applied strain with a slope of −3.16 kHz/$\mu\varepsilon$, as shown in FIGS. 8b and 8c. The polymer fiber has survived an axial strain (2% in this example) that is much larger than the breaking strain of a glass fiber (0.4%).

Figure 9:
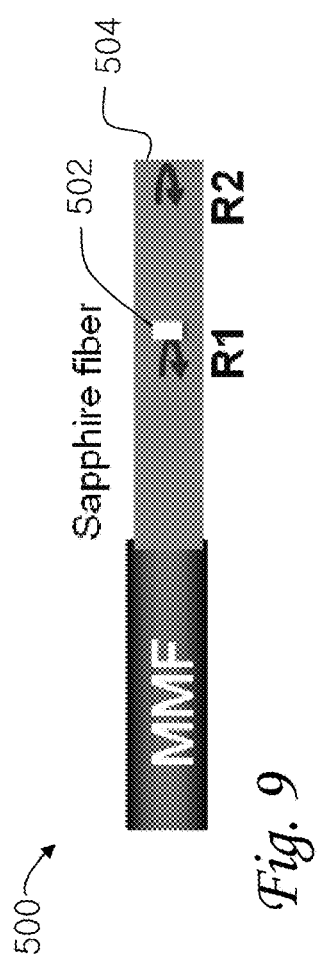
FIG. 9 is an elevation view of a sapphire optical fiber Fabry-Perot interferometer.
Figure 10:
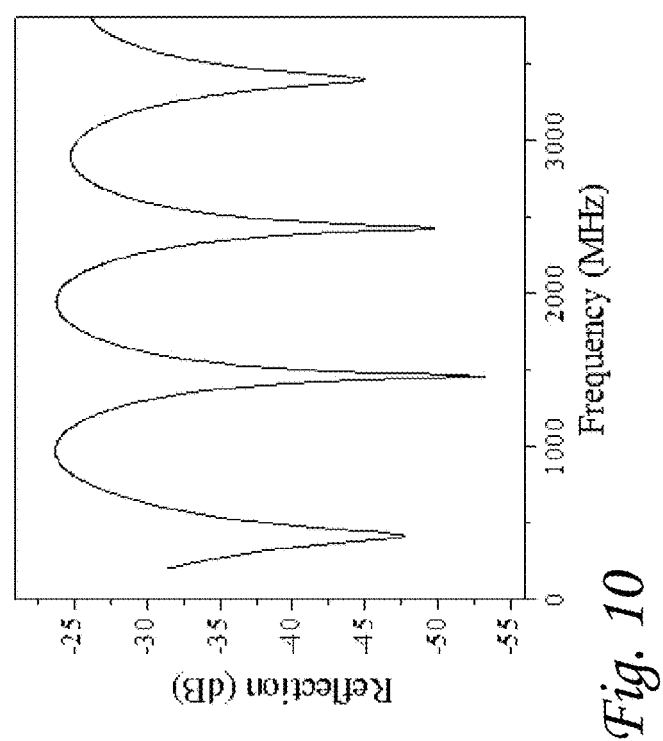
FIG. 10 is an interferogram of a sapphire optical fiber Fabry-Perot OCMI system.

An interferometer 500 of a sapphire optical fiber based OCMI-FPI system is shown in FIG. 9. The first reflection is from the interface 502 between the silica MMF and the sapphire fiber and the second reflection is from the interface 504 between the sapphire fiber and air at the far end. The resultant microwave interferogram of the sapphire optical fiber based OCMI-FPI system obtained using the interrogation setup illustrated in FIG. 2 is shown in FIG. 10. The sapphire fiber based OCMI-FPI system may be used for sensing in high temperatures because single crystal sapphire has a melting point above 2000 C. In addition, because the signal detection is synchronized with the microwave frequencies, the blackbody radiation of sapphire material in high temperatures can be drastically reduced.

Example 2

OCMI Based Michelson Interferometer

The optical Michelson interferometer (MI) first splits light into two paths by an optical beam splitter/combiner. The two light beams travel along a distance and are reflected back by two reflectors inserted into the two paths. The two reflected beams are then recombined at the beam splitter/combiner. The superposition of the two beams results in an interference signal that is a function of the optical path difference (OPD) between the two different paths. The MI interferometer can be implemented in both bulk optics and fiber optics. MIs are conventionally interrogated in optical domain. To obtain a high quality interference signal, the OPD has to be smaller than the coherence length of the light source used.

The conventional all-optical MI can be used to form an OCMI-MI system. As an example, the OCMI-MI system has an OPD of about 12 cm. The OCMI-MI system is interrogated using the setup illustrated in FIG. 2. A fiber optic MI 600 is illustrated in FIG. 11, where the beam splitter/combiner is a 3 dB 2×2 fiber coupler 602 and the two paths 604, 606 are two different fibers. The microwave interferogram of the OCMI-MI system is shown in FIG. 12, where the fringe visibility is over 30 dB and the free spectral range of the interferogram is about 800 MHz. The OCMI-MI system illustrated here uses single mode fiber in its implementation. Just like the OCMI-FPI system 200, the OCMI-MI system can be constructed using single mode and multimode optical fibers.

Example 3

OCMI Based Mach-Zehnder Interferometry System

The Mach-Zehnder interferometer (MZI) is another type of interferometer that has been widely used for sensing and monitoring. MZI has also found many applications in optical communications to construct modulators, wavelength division multiplexers (WDM), optical filters, etc. In a conventional all-optical MZI configuration, light is first split into two paths at a splitter. After propagating along two separate paths with a difference in length, the two lights are recombined at a combiner where the two light signals superimpose coherently to generate an interference signal in optical domain.

Figure 13:
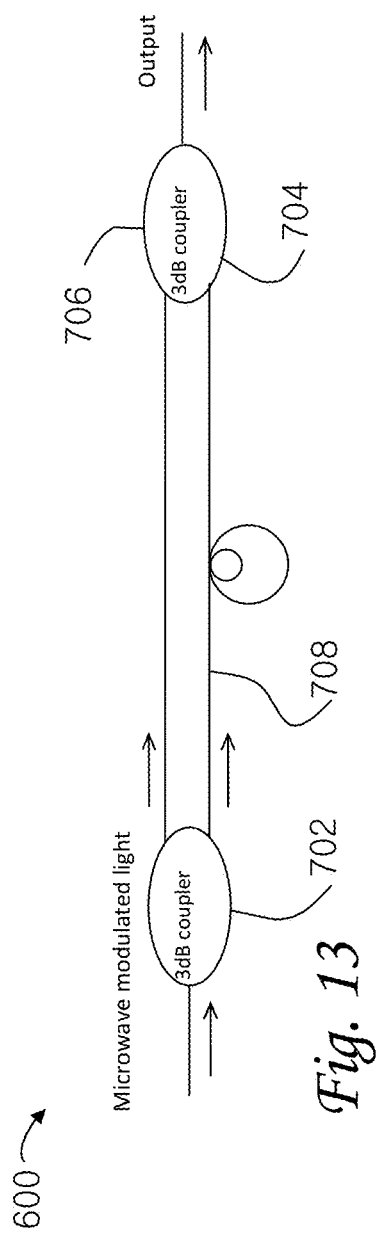
FIG. 13 is a schematic view of a Mach-Zender interferometer.
Figure 14:
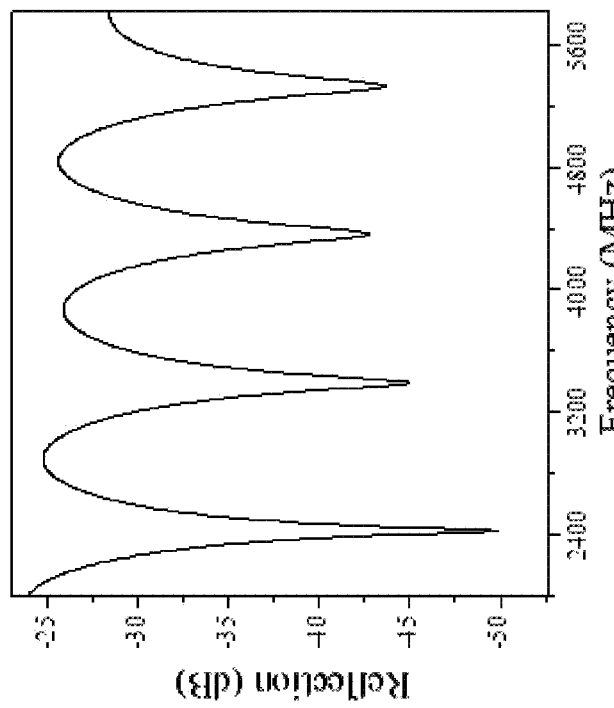
FIG. 14 is an interferogram of a Mach-Zender OCMI system.

An optical MZI 700 can be used to form an OCMI-MZI system, as shown in FIG. 13. First and second 3 dB fiber couplers 702, 704 are used to construct the interferometer. The first fiber coupler 702 splits input light into two different paths 706, 708 and the second fiber coupler 704 recombines the split lights. The OPD of the two paths 706, 708 can be made to be larger than the coherence length of the optical source and smaller than the coherence length of the microwave source. A high quality interference signal can thus be observed in the microwave domain, as shown in FIG. 14. The optical fiber used for constructing the OCMI-MZI system can be either single mode or multimode.

Distributed Optical Absorption and/or Emission Spectra Measurement OCMI System

Figure 15:
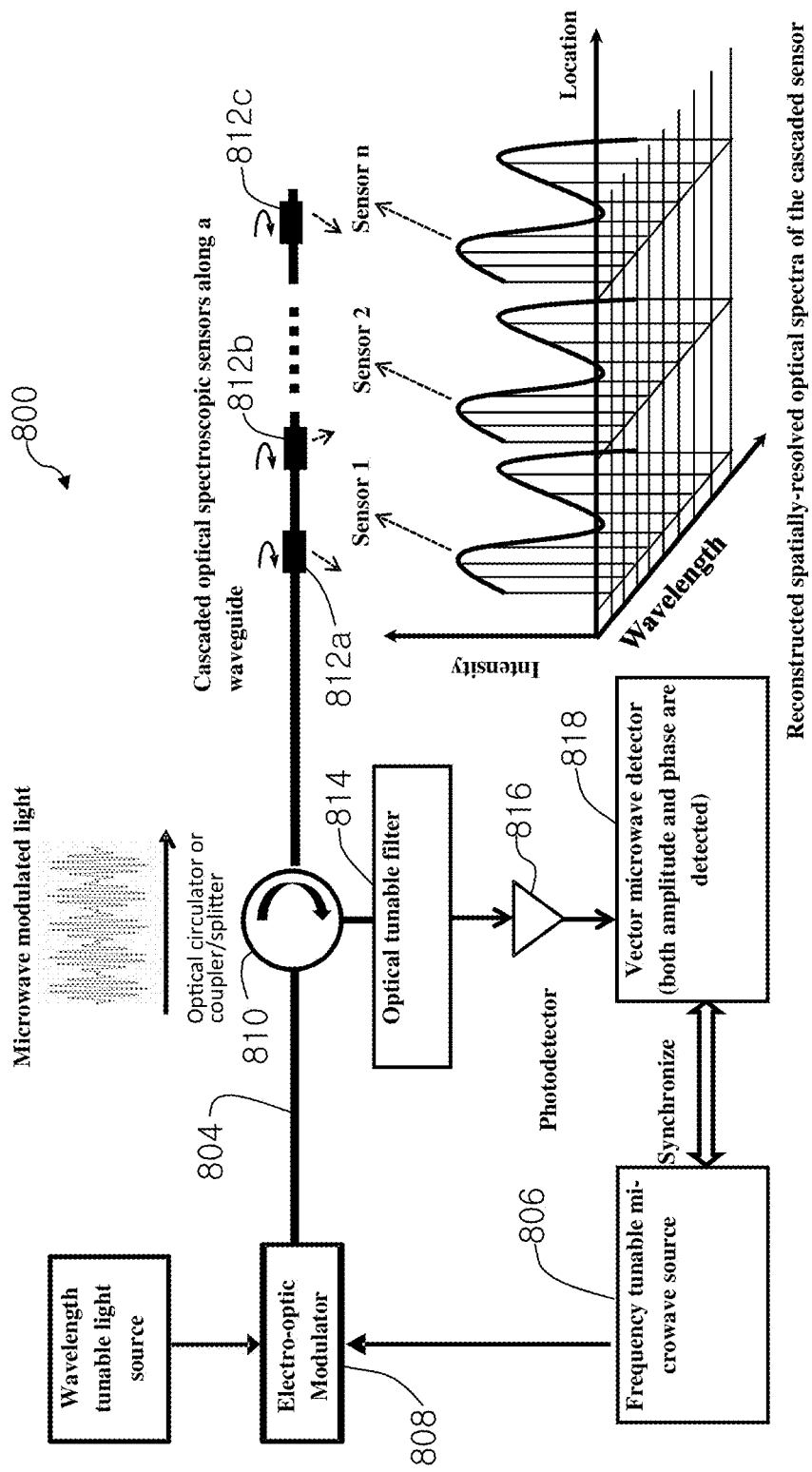
FIG. 15 is a schematic view of another OCMI system for distributed measurement of physical, chemical and biological at spatially different locations.

A distributed optical absorption and/or emission spectra measurement OCMI system 800 constructed in accordance with another embodiment of the invention includes a wavelength tunable light source 802, a wave guide 804, a frequency tunable microwave source 806, a modulator 808, an optical circulator 810, a number of optical spectroscopic sensors 812a,b,c, an optical tunable filter 814, a photodetector 816, and a vector microwave detector 818, as shown in FIG. 15.

The wavelength tunable light source 802 generates an optical carrier signal that can be tuned for scanning over an optical frequency range. The wavelength tunable light source 802 may be a wavelength tunable laser source or a combination of a broadband light source and an optical tunable filter.

The wave guide 804 is an optical fiber cable or similar medium as described above. Alternatively, the signals may travel in freespace (e.g., a vacuum, gas, liquid, solid, and biological material).

The frequency tunable microwave source 806 generates a microwave envelope signal that can be tuned for scanning over a microwave frequency range.

The modulator 808 is an electro-optic modulator or similar modulator that can modulate the amplitude, phase, or frequency of the optical carrier signal.

The optical circulator 810 directs the optical carrier signal and the microwave envelope signal from the sources 802, 806 and toward the sensors 812a,b,c. The optical circulator 810 also directs reflected light from the sensors 812a,b,c to the optical tunable filter 814. Alternatively an optical splitter or coupler can be used.

The optical spectroscopic sensors 812a,b,c are positioned along the waveguide 804. The sensors 812a,b,c can be absorption spectroscopic sensors or emission spectroscopic sensors. The sensors 812a,b,c change their absorption or emission spectrum pattern upon contacting target molecules of the physical, chemical, or biological property being measured. The optical carrier signal (and microwave envelope signal) reflects off of or interacts with the sensors 812a,b,c and travels back towards the optical circulator 810 in the same way as in the interferometers described above (e.g., by forming second, third, and $n^{th}$ number of signals travelling along second, third, and $n^{th}$ number of paths). The sensors 812a,b,c can be weak enough so that the optical signal can be transmitted over many sensors with extra reflections being negligible. Because any two reflectors (sensors 812a,b,c) can be chosen to form an OCMI interferogram, spatially continuous distributed sensing with no dark zones can be realized by consecutively selecting two adjacent reflectors along the waveguide 804. In addition, the base length of the interferometer can be varied by choosing any two arbitrary reflectors. As such, the gauge length can be flexibly reconfigured during measurement.

The optical tunable filter 814 filters out the light from the optical carrier signal by allowing only light of the selected frequency to pass therethrough.

The optical photodetector 816 converts the optical carrier signal and/or the microwave envelope signal into an electrical signal. The optical detection is synchronized with the microwave frequency by a phase lock loop (PLL) so that the amplitude and phase of the reflected signals can be resolved.

The vector microwave detector 818 (e.g., a vector network analyzer) receives and analyzes the electrical signal output by the optical photodetector 816. The vector microwave detector 818 measures and records the amplitude and phase of the electrical signal. The vector microwave detector 818 then scans the microwave envelope signal over the entire available microwave frequency range (i.e., the range spanned by the frequency tunable microwave source 816) to obtain the complex microwave spectrum with both amplitude and phase information therein. A complex Fourier transform is then applied to the spectrum to produce location resolved sensor information.

The system 800 can measure the physical, chemical, or biological property in two ways: optical absorption spectroscopy and optical emission spectroscopy. Optical absorption spectroscopy measures the optical absorption induced by the species or molecules of the specimen being studied. Optical absorption spectroscopy can be performed in all spectral ranges including ultraviolet (UV), visible, and infrared (IR) ranges. Optical emission spectroscopy measures and/or identifies chemical and biological species based on the excited emission spectrum of the species that is excited by an optical light. Fluorescence spectroscopy, Raman spectroscopy, and other forms of spectroscopy can be used to obtain measurable optical emissions. By tuning the optical wavelength of the light source or by changing the center wavelength of the optical tunable filter 814, the optical spectra (either absorption or emission spectrum) of the sensors 812$a,b,c$ are reconstructed and spatially resolved.

The present invention provides numerous advantages over conventional interferometry systems. For example, the optical interferometer can be designed to have sufficiently large optical path difference (OPD), and the spectral width of the optical carriers is sufficiently large. In other words, the OPD of the optical interferometer is much larger than the coherence length of the optical source so that no optical interference will be generated. On the other hand, the microwave bandwidth can be chosen to be small so that it has a coherence length that is sufficiently larger than the path difference of the interferometer. High quality interference signal can thus be observed in the microwave domain. The concept can be implemented on all types of optical interferometers such as Fabry-Perot interferometer (FPI), Fizeau interferometer, Michelson interferometer (MI), Mach-Zehnder interferometer (MZI) and Sagnac interferometer, etc.

Most of the advantages of optical interferometers can be inherited into OCMI such as reduced size, light weight, low attenuation over the entire modulation frequency range, and immunity to electromagnetic interference. Meanwhile, OCMI has many other unique features that conventional optical interferometry does not have, including:

1) The stringent requirements on surface qualify and fabrication precision on conventional optical interferometers can be drastically relieved on OCMI. The wavelength of microwave is much larger than that of an optical wave. In a sense, currently available micro/nano fabrication techniques can now easily satisfy the precision requirements.

2) The OCMI is independent to different types of optical waveguides/media. Single mode, multimode, highly-multimode are now the same to the microwave signal, because the difference in optics (e.g., dispersion and modal interference) cannot be resolved in the microwave scale. In other words, there is no difference between a multimode fiber and a single mode fiber seen by microwave.

3) The microwave interrogated system has very high resolution, potentially higher than that in optics. Microwave can easily resolve 1 Hz out of 10 GHz which will obtain the resolution of $\sim 10^{-10}$. In comparison, optics can resolve 1 pm out of 1.5 micrometer ($\sim 10^{-6}$).

4) OCMI uses coherent detection in which the modulation, detection and demodulation are all synchronized to a single radio frequency. Comparing DC detection in optics, coherent detection has much higher signal-to-noise ratio. Moreover, coherent detection can drastically eliminate blackbody radiation when the sensor is used in high temperatures.

5) The combination of microwave and optics has flexible choices of signal processing method and instrument. For instance, signals in time domain, frequency domain (optical frequency and radio frequency) or phase domain can be arbitrarily chosen for data processing; AM, FM, PM and even Code-domain (CDMA) can be used for instrumentation.

6) It is much easier to distinguish cascaded the microwave sensors that are separated in millimeter/centimeter scale to realize multiplexing and distributed sensing.

7) OCMI does not have the polarization fading issue that has been seen in the all-optical interferometers. In an OCMI, the interference is a result of coherent superposition of the microwave envelope. As such, the polarization status of the optical carrier wave does not affect the interference signal in microwave domain.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A system for measuring a physical, chemical, or biological property, the system comprising:

a carrier signal source for generating a first carrier signal and for transmitting the first carrier signal along a first path;

an envelope signal source for generating a first microwave envelope signal;

a modulator configured to modulate the first carrier signal with the first envelope signal so that the first envelope signal travels along the first path via the first carrier signal;

an interferometer placed along the first path and configured to split the first carrier signal and the first envelope signal into at least a second carrier signal and a second envelope signal travelling along a second path and a third carrier signal and a third envelope signal travelling along a third path, the second path and the third path cooperatively defining a path difference corresponding to a difference in length between the third path and the second path, the second carrier signal and the third carrier signal combining with each other in a fourth path to form a fourth carrier signal and the second envelope signal and the third envelope signal combining with each other in the fourth path to form a fourth envelope signal, the fourth envelope signal having at least one feature resulting from the path difference;

a detector positioned along the fourth path and configured to convert the fourth envelope signal into an electronic signal having at least one feature corresponding to the at least one feature of the fourth envelope signal; and an analyzer for extracting the at least one feature of the electronic signal, the at least one feature of the electronic signal equating to a value of the physical, chemical, or biological property being measured.

2. The system of claim 1, wherein the path difference is longer than a coherence length of the carrier signal source and is shorter than a coherence length of the envelope signal source.

3. The system of claim 1, further comprising an optical wave guide for directing the first carrier signal along the first path, wherein the carrier signal source is an optical source, the first, second, third, and fourth carrier signals are optical carrier signals, the envelope signal source is a microwave source, the first, second, third, and fourth envelope signals are microwave envelope signals, the modulator is a microwave modulator, the interferometer is an optical interferometer, the path difference is an optical path difference, and the detector is a photodetector.

4. The system of claim 3, wherein the microwave envelope signals have a predetermined microwave frequency range, the at least one feature of the fourth microwave envelope signal being a plurality of amplitudes and phases over the predetermined microwave frequency range resulting from the optical path difference, the at least one feature of the electronic signal including a plurality of amplitudes and phases corresponding to the amplitudes and phases of the fourth microwave envelope signal, the analyzer being configured to extract the plurality of amplitudes and phases of the electronic signal over the predetermined microwave frequency range so as to form an amplitude pattern and a phase pattern, at least one feature of the amplitude pattern or the phase pattern equating to a value of the physical, chemical, or biological property being measured.

5. The system of claim 4, wherein the analyzer is configured to extract a change in the at least one feature of the amplitude pattern and phase pattern, the change equating to a change in the value of the physical, chemical, or biological property being measured.

6. The system of claim 5, wherein the property being measured is strain and the change in the at least one feature of the amplitude pattern or phase pattern is a shift along the frequency domain, the shift linearly equating to a change in strain.

7. The system of claim 3, wherein the microwave envelope signals have a predetermined microwave frequency, the at least one feature of the fourth microwave envelope signal being an amplitude or phase resulting from the optical path difference, the at least one feature of the electronic signal being an amplitude or phase corresponding to the amplitude or phase of the fourth microwave envelope signal, the analyzer being configured to extract the amplitude or phase of the electronic signal, the amplitude or phase of the electronic signal equating to a value of the physical, chemical, or biological property being measured.

8. The system of claim 3, wherein the optical source is a broadband light source for minimizing the coherence length of the optical source.

9. The system of claim 3, wherein the microwave modulator is an electro-optic modulator (EOM) configured to modulate the amplitude, frequency or phase of the first optical carrier signal in the microwave domain.

10. The system of claim 3, wherein the microwave modulator is a direct current modulator configured to change a driving electric current of the optical source for modulating the first optical carrier signal.

11. The system of claim 3, further comprising a direct current biaser and a radio frequency (RF) amplifier, the biaser and the amplifier cooperatively being configured to maximize a modulation index of the first optical carrier signal when the first optical carrier signal is modulated by the microwave modulator.

12. The system of claim 3, wherein the optical interferometer is an intrinsic Fabry-Perot interferometer, an extrinsic Fabry-Perot interferometer, a Michelson interferometer, a Mach-Zehnder interferometer, a Fizeau interferometer, or a Sagnac interferometer.

13. The system of claim 3, wherein the waveguide is a fiber optic cable and the optical interferometer is a Fabry-Perot interferometer (FPI) comprising a first optical partial reflector and a second optical partial reflector spaced from the first optical partial reflector a distance equal to one half of the optical path difference, the first optical partial reflector being configured to split the first optical carrier signal into the second optical carrier signal and the third optical carrier signal and being configured to reflect the second optical carrier signal and allow the third optical carrier signal to pass therethrough, wherein the system further comprises a fiber circulator for directing the first optical carrier signal into the optical interferometer and for directing the second optical carrier signal and the third optical carrier signal into the photodetector.

14. The system of claim 13, wherein the analyzer is configured to apply a complex inverse Fourier transform to the amplitude pattern and phase pattern of the electronic signal to extract a reflection of the second optical carrier signal and a reflection of the third optical carrier signal as a function of time.

15. A method of measuring a physical, chemical, or biological property, the method comprising the steps of:
generating a first optical carrier signal having a predetermined optical frequency range via an optical source;
transmitting the first optical carrier signal along a first path via a waveguide;
generating a first microwave envelope signal having a predetermined microwave frequency range via a microwave source;
modulating the first optical carrier signal with the first microwave envelope signal via a microwave modulator so that the first microwave envelope signal travels along the first path via the first optical carrier signal;
splitting the first optical carrier signal and the first microwave envelope signal into at least a second optical carrier signal and a second microwave envelope signal travelling along a second path and a third optical carrier signal and a third microwave envelope signal travelling along a third path via an optical interferometer, the second path and the third path cooperatively defining an optical path difference corresponding to a difference in length between the third path and the second path;
modifying the second optical carrier signal to have a plurality of amplitudes via a physical, chemical, or biological property being measured at a first location;
modifying the third optical carrier signal to have a plurality of amplitudes via the physical, chemical, or biological property being measured at a second location, the second optical carrier signal and the third optical carrier signal combining with each other in a final path to form a final optical carrier signal and the second microwave envelope signal and the third microwave envelope signal combining with each other in the final path to form a final microwave envelope signal, the final optical carrier signal having a plurality of amplitudes over the predetermined optical frequency range resulting from the interactions with the physical, chemical, or biological property being measured in the second and third paths, the final microwave envelope signal having a plurality of amplitudes and phases over the predetermined microwave frequency range resulting from the optical path difference;

converting the final optical carrier signal and the final microwave envelope signal into an electronic signal via a photodetector, the electronic signal having a plurality of optical amplitudes corresponding to the amplitudes of the final optical carrier signal and a plurality of microwave amplitudes and phases corresponding to the amplitudes of the final microwave envelope signal;

extracting the plurality of optical amplitudes of the electronic signal over the predetermined optical frequency range via an analyzer so as to form a first optical amplitude pattern corresponding to the second optical carrier signal and a second optical amplitude pattern corresponding to the third optical carrier signal, at least one feature of the first optical amplitude pattern corresponding to a value of the physical, chemical, or biological property being measured at the first location and at least one feature of the second optical amplitude pattern corresponding to a value of the physical, chemical, or biological property being measured at the second location; and extracting the plurality of microwave amplitudes and microwave phases of the electronic signal over the predetermined microwave frequency range via the analyzer so as to form a microwave amplitude and phase pattern, at least one feature of the microwave amplitude and phase pattern corresponding to the first location and at least one feature of the microwave amplitude and phase pattern corresponding to the second location.

16. The method of claim 15, wherein the step of modulating the first optical carrier signal includes modulating an amplitude, a phase, or a frequency of the first optical carrier signal in the microwave domain.

17. The method of claim 15, wherein each path includes an optical spectroscopic sensor.

\* \* \* \* \*